(12) United States Patent
Nukui

(10) Patent No.: US 7,856,133 B2
(45) Date of Patent: Dec. 21, 2010

(54) X-RAY ATTENUATION CORRECTION METHOD, IMAGE GENERATING APPARATUS, X-RAY CT APPARATUS, AND IMAGE GENERATING METHOD

(75) Inventor: Masatake Nukui, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1036 days.

(21) Appl. No.: 11/612,566

(22) Filed: Dec. 19, 2006

(65) Prior Publication Data

US 2007/0140416 A1 Jun. 21, 2007

(30) Foreign Application Priority Data

Dec. 21, 2005 (JP) .............................. 2005-367389
Jun. 28, 2006 (JP) .............................. 2006-177692

(51) Int. Cl.
*G06K 9/00* (2006.01)

(52) U.S. Cl. ........................ 382/131; 382/275; 378/98.4

(58) Field of Classification Search ................. 382/128, 382/131, 132, 199, 275; 378/7, 70, 86, 98.4
See application file for complete search history.

(56) References Cited

U.S. PATENT DOCUMENTS

| 6,094,467 | A | 7/2000 | Gayer et al. | 378/4 |
| 6,819,734 | B2 | 11/2004 | Raupach | 378/4 |
| 2003/0103595 | A1* | 6/2003 | Raupach | 378/4 |
| 2005/0053191 | A1 | 3/2005 | Gohno et al. | 378/19 |

FOREIGN PATENT DOCUMENTS

| JP | 05-094515 A | 4/1993 |
| JP | 06337933 A | 12/1994 |
| JP | 07123248 A | 5/1995 |
| JP | 2003102719 A | 8/2003 |
| JP | 2005095397 A | 4/2005 |

OTHER PUBLICATIONS

International Search Report for Application NL 1033109, dated Aug. 8, 2007.
Glover G H: "Compton scatter effects in CT reconstructions" Medical Physics, AIP, Melville, NY, US, Nov. 1962.
Joseph P M et al.: "The effects of scatter in x-ray computed tomography" Medical Physics, AIP, Melville, NY, US, Jul. 1982.
Chinese Patent Office, Translated First Office Action and Text or First Office Action, Nov. 20, 2009, 8 pages.
Japan Patent Office, Notice of Reasons for Rejection for Publication No. 2006-177692, Sep. 14, 2010, 3 pages.

* cited by examiner

*Primary Examiner*—Andrew W Johns
(74) *Attorney, Agent, or Firm*—Armstrong Teasdale LLP

(57) ABSTRACT

The present invention provides an X-ray attenuation correction method, image generating apparatus, X-ray CT apparatus, and image generating method for correcting for the attenuation of X-ray beam at the boundary where the X-ray absorption rate of a subject is changing. Boundary information comprised of the boundary position where the X-ray absorption rate is changing and the magnitude of change is extracted from the projection information of the subject, then the boundary information is used to multiply the amount of scattered X-ray by the amount corresponding to the magnitude of change at the boundary position, to correct for the attenuation of X-ray at the boundary position. The attenuation of X-ray at the boundary position may be corrected for along with the scattered X-ray correction of the projection information, allowing alleviating artifacts developed in a tomographic image.

18 Claims, 11 Drawing Sheets

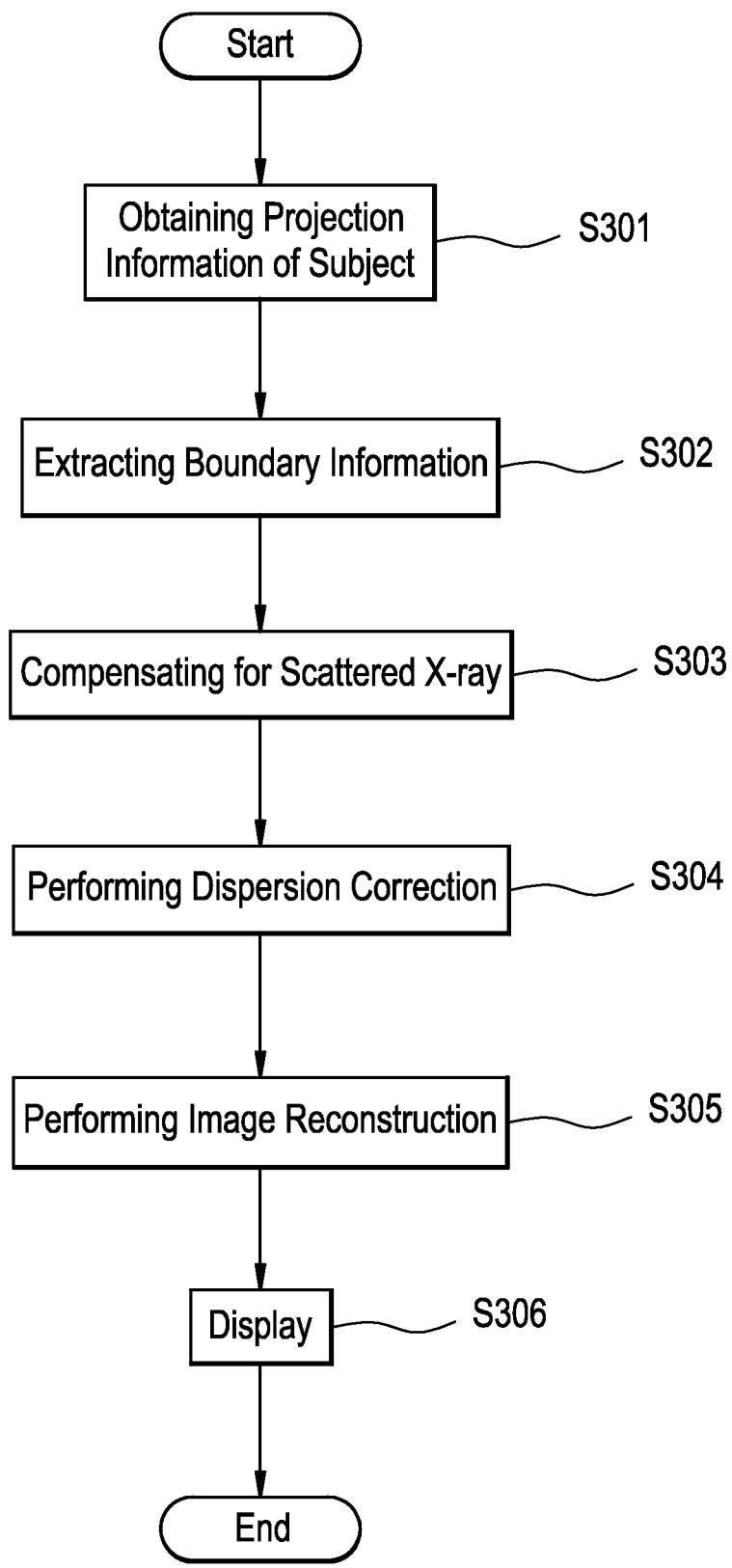

Tomographic image IMG(x,y)

Boundary image BIMG(x,y)

Boundary projection value (BD(i, j))

Channel number (i)

Tomographic image IMG(x,y)

Scattered X-ray Image SIMG (x,y)

Subtracted image DIMG (x,y)

_US 7,856,133 B2_

X-RAY ATTENUATION CORRECTION METHOD, IMAGE GENERATING APPARATUS, X-RAY CT APPARATUS, AND IMAGE GENERATING METHOD

CROSS REFERENCE TO RELATED APPLICATIONS

This application claims the benefit of Japanese Application No. 2005-367389 filed Dec. 21, 2005 and Japanese Application No. 2006-177692 filed Jun. 26, 2006.

BACKGROUND OF THE INVENTION

The present invention relates to an X-ray attenuation correction method for correcting for the attenuation of X-ray beam emitted to a subject, an image generating apparatus, an X-ray CT apparatus, and an image generating method.

The X-ray CT apparatuses have been widely used these days, and the image quality requirement for tomographic image information obtained by an X-ray CT apparatus is continuously becoming finer. There are methods for improving the image quality of the X-ray CT images, which include for example the correction of the dispersed X-ray generated within a subject.

In the above method the amount of scattered X-ray theoretically or experimentally determined is eliminated from the projection information of the subject. The projection information which is the basis of the image reconstruction is configured so as to be comprised of solely the transmitted X-ray beam.

The amount of scattered X-ray from the subject increases in relation to the transmission distance of the X-ray beam passing through the subject (referred to as projection length herein below). Therefore the projection length should be considered when correcting for the scattered X-ray, so that the amount of scattered X-ray to be corrected for must be larger when the projection length is longer, namely, the subject has a larger thickness in the direction of the projection.

However, in accordance with the background art described above, the correction of the scattered X-ray based on the projection length is not sufficient. More specifically, when there is a boundary changing the absorption rate of X-ray on the path of the X-ray beam transmission, the X-ray beam will be attenuated on the boundary. The attenuation is a phenomenon different from the dispersion of X-ray beam seen in a uniform medium, which cannot be corrected for by considering the projection length.

The attenuation of the X-ray beam on the boundary, in particular, may generate artifacts on an image in vicinity of the boundary where the X-ray absorption rate is changing, during the formation of a tomographic image by device of image reconstruction. The artifact may be a cause of degrading the image quality of tomographic image, thus this is never preferable.

Therefore, it is important to achieve an X-ray attenuation correction method for correcting for the X-ray beam attenuation on the boundary where the X-ray absorption rate of the subject is changing, and an X-ray CT apparatus.

SUMMARY OF THE INVENTION

The present invention has been made in view of solving the problem seen in the background art described above, and has a subject to provide an X-ray attenuation correction method for correcting for the attenuation of X-ray beam on the boundary where the X-ray absorption rate of the subject is changing, and an X-ray CT apparatus.

In order to solve the problem described above and to achieve the subject, the present invention provides an X-ray attenuation correction method in accordance with first aspect of the present invention, comprising the steps of: extracting boundary information including boundary positional information of a boundary position where X-ray absorption rate is changing and magnitude information indicative of magnitude of said change, by using X-ray projection information of a subject or tomographic image information being generated by image reconstruction of said projection information; and correcting X-ray attenuation of said boundary position included in said projection information or said tomographic image information by using said boundary information.

The present invention in accordance with the first aspect allows correcting for the X-ray attenuation seen at the boundary position, where the X-ray absorption rate is changing, included in the X-ray projection information or tomographic image information.

In a second aspect, the present invention provides an X-ray attenuation correction method in accordance with the first aspect, wherein said step of extracting boundary information includes steps of: differentiating projection value of said projection information in the direction corresponding to the channel direction and/or row direction of an X-ray detector which obtains said projection information; extracting a position where the magnitude of said differentiated value exceeds a threshold as said boundary position information; and extracting the magnitude of said differentiated value as said magnitude information.

The present invention in accordance with the second aspect allows the position where the projection value changes significantly to be set as boundary position where the X-ray absorption rate is changing.

In a third aspect, the present invention provides an X-ray attenuation correction method in accordance with the X-ray attenuation correction method of the first aspect, wherein said step of extracting boundary information includes steps of: differentiating the tomographic image of said tomographic image information; performing absolute value operation of said differentiated image to generate a boundary image; and extracting said boundary information using said boundary image.

The present invention in accordance with the third aspect allows determining the boundary image from the tomographic image information.

In fourth aspect, the present invention provides an X-ray attenuation correction method in accordance with the X-ray attenuation correction method of the third aspect, wherein said step of extracting boundary information includes the steps of: calculating boundary projection information using said boundary image; extracting as boundary position information a position where the boundary projection value of said boundary projection information is not zero; and extracting said boundary projection value as said magnitude information.

The present invention in accordance with the fourth aspect allows determining the boundary position and the magnitude of change from the boundary image.

In fifth aspect, the present invention provides an X-ray attenuation correction method in accordance with the X-ray attenuation correction method of any one of first to fourth aspect, wherein said step of correcting X-ray attenuation includes a step of correcting by using a gain function having a multidimensional function of said projection information.

The present invention in accordance with the fifth aspect allows converting the magnitude of change into a value appropriate for the dispersion X-ray correction.

In a sixth aspect the present invention provides an X-ray attenuation correction method in accordance with the X-ray attenuation correction method of the fifth aspect, wherein said step of correcting X-ray attenuation includes steps of multiplying the amount of scattered X-ray at said boundary position in said projection information by the function value of said gain function, then subtracting said multiplied amount of scattered X-ray from said projection information.

The present invention in accordance with the sixth aspect allows the feasible correction of X-ray attenuation at the boundary position by adding some correction to the amount of scattered X-ray.

In a seventh aspect the present invention provides an X-ray attenuation correction method in accordance with the X-ray attenuation correction method of fifth aspect, wherein said step of correcting X-ray attenuation includes steps of multiplying the amount of scattered X-ray at said boundary position in said tomographic image information by the function value of said gain function, performing image reconstruction of said multiplied amount of scattered X-ray, and then subtracting the amount from said tomographic image information.

The present invention in accordance with the seventh aspect allows feasibly the correction of X-ray attenuation at the boundary position by subtracting the corrected amount of scattered X-ray image reconstructed from the tomographic image.

In a eighth aspect the present invention provides an image generating apparatus, for generating a tomographic image in an X-ray CT apparatus, comprising: device for extracting boundary information including boundary position information of the boundary position where X-ray absorption rate is changing and magnitude information indicative of magnitude of said change, by using X-ray projection information of a subject or tomographic image information generated by performing image reconstruction of said projection information; and device for correcting X-ray attenuation of said boundary position included in said projection information or said tomographic image information by using said boundary information.

The present invention in accordance with the eighth aspect allows correcting for X-ray attenuation seen at the boundary position, where X-ray absorption rate is changing, included in X-ray projection information or tomographic image information.

In a ninth aspect the present invention provides an image generating apparatus in accordance with the image generating apparatus of the eighth aspect, wherein said device for extracting boundary information includes device for differentiating a projection value of said projection information in the direction corresponding to the channel direction and/or row direction of an X-ray detector which obtains said projection information, and device for extracting a position where the magnitude of said differentiated value exceeds a threshold as said boundary position information.

The present invention in accordance with the ninth aspect allows determining the position where the projection value significantly changes as the boundary position where the X-ray absorption rate is changing.

In a tenth aspect the present invention provides an image generating apparatus in accordance with the image generating apparatus of the eighth aspect, wherein said device for extracting boundary information includes device for differentiating a tomographic image of said tomographic image information, device for performing the absolute value operation on said differentiated image to generate a boundary image, and device for extracting said boundary information by using said boundary image.

The present invention in accordance with the tenth aspect allows determining the boundary image from tomographic image information.

In an eleventh aspect the present invention provides an image generating apparatus in accordance with the image generating apparatus of the tenth aspect, wherein said device for extracting boundary information includes device for calculating boundary projection information by using said boundary image, device for extracting as boundary position information a position where boundary projection value of said boundary projection information is not zero, and device for extracting said boundary projection value as said magnitude information.

The present invention in accordance with the eleventh aspect allows determining the boundary position and the magnitude of change from the boundary image.

In a twelfth aspect the present invention provides an image generating apparatus in accordance with the image generating apparatus selected from any one of eighth to eleventh aspect, wherein said device for correcting X-ray attenuation includes device for correcting by using a gain function having a multidimensional function of said magnitude information.

The present invention in accordance with the twelfth aspect allows converting the magnitude of change into a value appropriate for dispersion X-ray correction.

In a thirteenth aspect the present invention provides an image generating apparatus in accordance with the image generating apparatus of the twelfth aspect, wherein said device for correcting X-ray attenuation includes a device for correcting by multiplying the amount of scattered X-ray at said boundary position in said projection information by a function value of said gain function, and subtracting said multiplied amount of scattered X-ray from said projection information.

The present invention in accordance with the thirteenth aspect allows feasibly the correction of X-ray attenuation at the boundary position by adding the correction for the amount of scattered X-ray.

In a fourteenth aspect the present invention provides an image generating apparatus in accordance with the image generating apparatus of the twelfth aspect, wherein said device for correcting X-ray attenuation includes a device for correcting by multiplying the amount of scattered X-ray at said boundary position in said tomographic image information by a function value of said gain function, performing image reconstruction of said multiplied amount of scattered X-ray, and subtracting the amount from said tomographic image information.

The present invention in accordance with the fourteenth aspect allows feasibly the correction of X-ray attenuation at the boundary position by subtracting the corrected amount of scattered X-ray image reconstructed from the tomographic image information.

In a fifteenth aspect the present invention provides an X-ray CT apparatus, which comprises: an X-ray data acquisition device including an X-ray generator and an X-ray detector placed in opposition to said X-ray generator for acquiring X-ray projection data by relatively rotating said X-ray generator and said X-ray detector around a subject; and an image information generating device for generating image information of the subject using said X-ray projection data; wherein said image generating device includes: a device for extracting boundary information including boundary position information of the boundary position where X-ray absorption rate is changing and magnitude information indicative of magnitude of said change, by using X-ray projection information of a subject or tomographic image information generated by performing image reconstruction of said projection information; and a device for correcting X-ray attenuation of said boundary position included in said projection information or said tomographic image information by using said boundary information.

The present invention in accordance with the fifteenth aspect allows correcting for X-ray attenuation seen at the boundary position included in the X-ray projection information or tomographic image information, where the X-ray absorption rate is changing.

In a sixteenth aspect the present invention provides an X-ray CT apparatus in accordance with the X-ray CT apparatus of the fifteenth aspect wherein said device for extracting boundary information includes a device for differentiating a projection value of said projection information in the direction corresponding to the channel direction and/or row direction of an X-ray detector which obtains said projection information, and a device for extracting a position where the magnitude of said differentiated value exceeds a threshold as said boundary position information.

The present invention in accordance with the sixteenth aspect allows determining the position where the projection value significantly changes as the boundary position where the X-ray absorption rate is changing.

In a seventeenth aspect the present invention provides an X-ray CT apparatus in accordance with the X-ray CT apparatus of the fifteenth aspect, wherein said device for extracting boundary information includes a device for differentiating a tomographic image of said tomographic image information, a device for performing the absolute value operation on said differentiated image to generate a boundary image, and a device for extract said boundary information using said boundary image.

The present invention in accordance with the seventeenth aspect allows determining the boundary image from the tomographic image information.

In an eighteenth aspect the present invention provides an X-ray CT apparatus in accordance with the X-ray CT apparatus of the seventeenth aspect, wherein said device for extracting boundary information includes a device for calculating boundary projection information by using said boundary image, a device for extracting as boundary position information a position where boundary projection value of said boundary projection information is not zero, and a device for extracting said boundary projection value as said magnitude information.

The present invention in accordance with the eighteenth aspect allows determining the boundary position and the magnitude of change from the boundary image.

In a nineteenth aspect the present invention provides an image generating method for generating a tomographic image in an X-ray CT apparatus the image generating method comprising the step of differentiating X-ray projection information of a subject or tomographic image information generated by the image reconstruction of said projection information, for extracting boundary information including the boundary position information of boundary position where the X-ray absorption rate is changing and magnitude information indicative of the magnitude of said change.

The present invention in accordance with the nineteenth aspect allows correcting for X-ray attenuation seen at the boundary position, where the X-ray absorption rate is changing, included in X-ray projection information or tomographic image information.

In accordance with the present invention, X-ray attenuation seen at the boundary position, where the X-ray absorption rate is changing, included in projection information or tomographic image information, is corrected for included in the scattered X-ray correction. This allows more accurate scattered X-ray correction, alleviating artifacts in the tomographic image caused by the X-ray attenuation at the boundary position, and obtaining a tomographic image of higher image quality.

BRIEF DESCRIPTION OF THE DRAWINGS

FIG. 3 is a flow chart illustrating the operation of the X-ray attenuation correction in accordance with first preferred embodiment of the present invention;

DETAILED DESCRIPTION OF THE INVENTION

Best modes for carrying out the X-ray attenuation correction method and X-ray CT apparatus in accordance with the present invention will be described in greater details with reference to the accompanying drawings herein below. It should be noted here that the best mode for carrying out the invention is not to be considered to limit the invention.

First Embodiment

Figure 1:
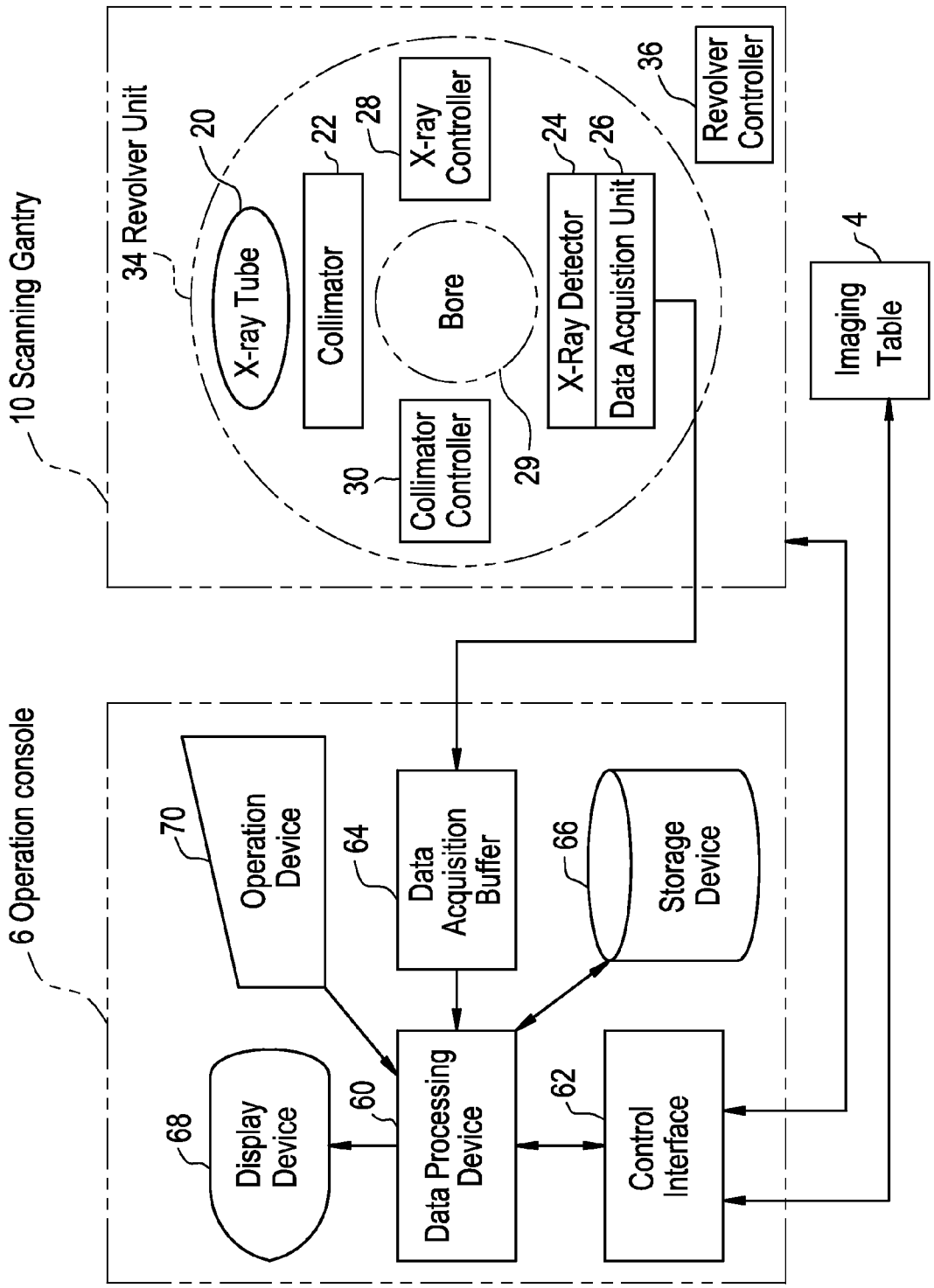
FIG. 1 is a schematic block diagram illustrating the overview of an X-ray CT apparatus.

Now the overview of an X-ray CT apparatus in accordance with the first preferred embodiment of the present invention will be described. Now referring to FIG. 1, there is shown a schematic block diagram of an X-ray CT apparatus. As shown in FIG. 1, the apparatus includes a scanning gantry 10, an operation console 6, and an imaging table 4.

The scanning gantry 10 includes an X-ray tube 20. The X-ray not shown in the figure but emitted from the X-ray tube 20, which is an X-ray generator, is shaped to an X-ray cone beam by a collimator 22 to have for example a fan shape with a certain thickness, and will be transmitted to an X-ray detector 24 placed in opposition to the X-ray tube 20.

The X-ray detector 24 has a plurality of scintillators arrayed as a matrix in the direction of expansion of the fan beam X-ray. The X-ray detector 24 is a multichannel detector having a plurality of scintillators arrayed in a matrix configuration with a certain width.

The X-ray detector 24 forms as whole an X-ray incident plane which is concaved. The X-ray detector 24 may be comprised of scintillators each made from inorganic crystal and photodiodes which serve as photoelectric transducer.

To the X-ray detector 24 a data acquisition unit 26 is connected. The data acquisition unit 26 acquires the detection information from each scintillator of the X-ray detector 24. The transmission of X-ray from the X-ray tube 20 is controlled by an X-ray controller 28. The connection between the X-ray tube 20 and the X-ray controller 28, the connection between the collimator 22 and a collimator controller 30 are not shown in the figure. The collimator 22 is controlled by the collimator controller 30.

These members from the X-ray tube 20 to the collimator controller 30 are mounted on a revolver unit 34 of the scanning gantry 10. A subject or a phantom is placed on the imaging table 4 in a bore 29 placed in the center of the revolver unit 34. The revolver unit 34 revolves under the control of a revolver controller 36, in order to emit X-ray from the X-ray tube 20, and to detect X-ray transmitted through the subject and phantom at the X-ray detector 24 as projection information comprised of view numbers (j, herein below) corresponding to the revolving angle and the channel number (i, herein below) of the X-ray detector array in the revolving direction. The connection between the revolver unit 34 and the revolver controller 36 is omitted in the figure.

The operation console 6 has a data processing device 60. The data processing device 60 may be comprised of a computer. The data processing device 60 is connected with a control interface 62. To the control interface 62 the scanning gantry 10 is connected. The data processing device 60 controls the scanning gantry 10 through the control interface 62.

The data acquisition unit 26, the X-ray controller 28, the collimator controller 30, and the revolver controller 36 within the scanning gantry 10 are controlled through the control interface 62. The individual connection between these units and the control interface 62 is not shown in the figure for the sake of clarity.

To the data processing device 60 a data acquisition buffer 64 is connected. To the data acquisition buffer 64 the data acquisition unit 26 of the scanning gantry 10 is connected. The data acquired by the data acquisition unit 26 is input through the data acquisition buffer 64 to the data processing device 60.

The data processing device 60 performs image reconstruction using the transmission X-ray signal gathered through the data acquisition buffer 64, namely the projection information. To the data processing device 60 a storage device 66 is connected. The storage device 66 stores projection information acquired into the data acquisition buffer 64 and the reconstructed tomographic image information as well as program for achieving a function of the apparatus.

To the data processing device 60 a display device 68 and an operation device 70 are connected. The display device 68 displays tomographic image information and other information output from the data processing device 60. The operation device 70 is operated by an operator to input various instructions and information to the data processing device 60. The operator uses the display device 68 and the operation device 70 to operate interactively the apparatus. The scanning gantry 10, the imaging table 4, and the operation console 6 images the subject or phantom to obtain a tomographic image.

Figure 2:
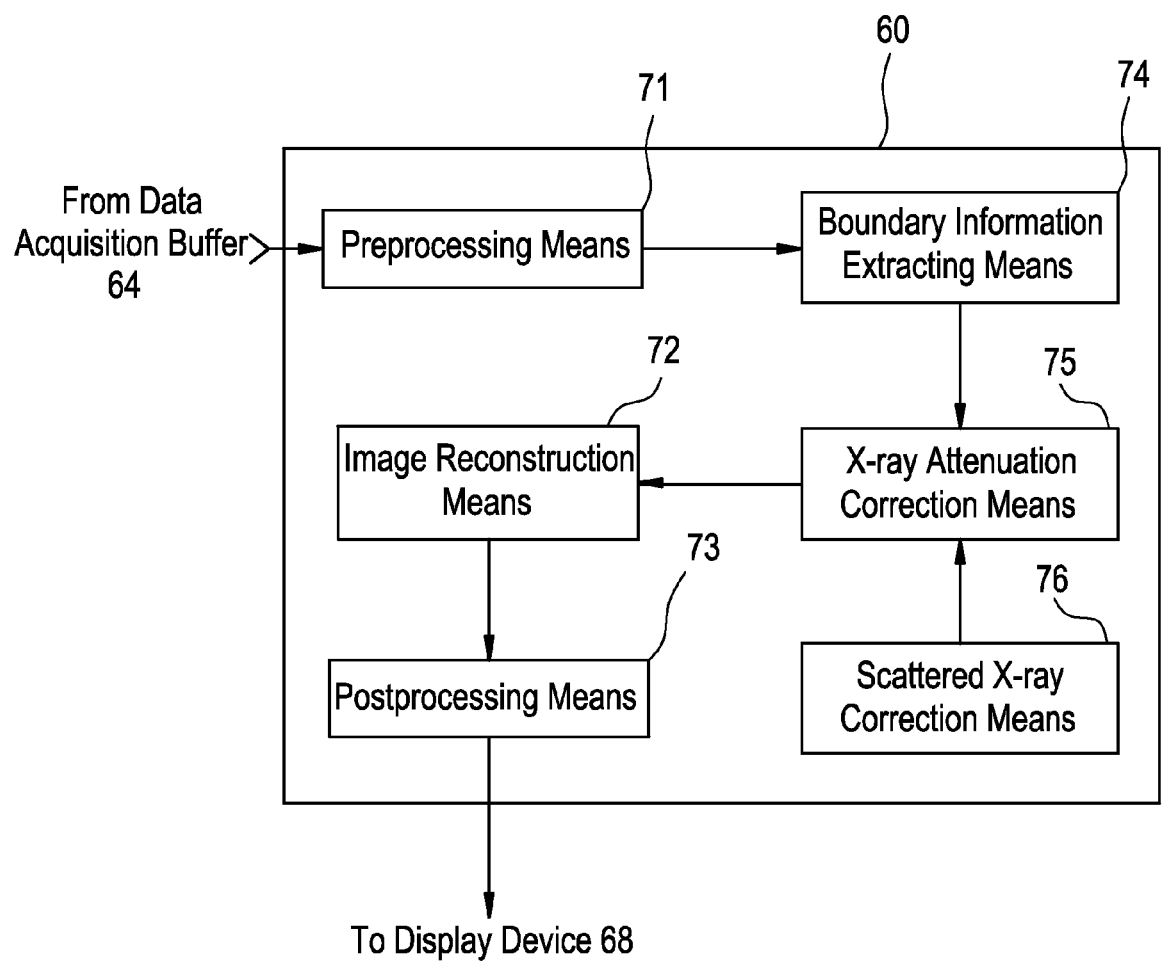
FIG. 2 is a functional schematic block diagram illustrating the functional arrangement of a data processing unit in accordance with first preferred embodiment of the present invention.

Now referring to FIG. 2 there is shown a functional block diagram indicating functional configuration of the data processing device 60. The data processing device 60 includes a preprocessing device 71, an image reconstruction device 72, a postprocessing device 73, a boundary information extracting device 74, an X-ray attenuation correction device 75, and a scattered X-ray correction device 76. The data processing device 60 is an exemplary embodiment of the image generating apparatus in accordance with the present invention.

The preprocessing device 71 performs an offset correction, and X-ray detector sensitivity correction to the projection information input from the data acquisition buffer 64.

The image reconstruction device 72 uses the preprocessed projection information P (i, j) for the image reconstruction to generate tomographic image information. The image reconstruction uses the FBR (filtered back projection) method for example when the projection information is acquired by using an axial scan or a helical scan. Further, the projection information having thickness may be treated as volume data to apply a three-dimensional image reconstruction method.

The postprocessing device 73 performs a postprocessing such as CT value conversion of the tomographic image information. The tomographic image information having postprocessing applied will be transferred to the display device 68.

The boundary information extracting device 74 determines from the preprocessed projection information P (i, j) the boundary information comprised of boundary position information of the boundary position where the X-ray absorption rate is discontinuously changing and of magnitude information indicative of the magnitude of the changing of X-ray absorption rate. The boundary information extracting device 74 has a differentiation computation device for differentiating the projection information in the direction corresponding to the channel direction of the X-ray detector (referred to as channel direction herein below). When the differentiation value exceeds a threshold it determines the boundary position. Given the projection value P (i, j) at the position of view number j and channel number i, the magnitude of the differentiation value D may be determined by $$|D(i,j)|=|[P(i+\Delta i,j)-P(i,j)]/\Delta i|,$$

and the boundary position may be the position of channel number $$|D(i,j)|>th, \text{ where th is the threshold.}$$

The scattered X-ray correction device 76 calculates the amount of scattered X-ray S (i, j) for a view number and for a channel number, included in the projection information. The amount of scattered X-ray S (i, j) may be calculated based on the scattered X-ray information obtained by using a phantom, and the precision is further improved by considering the projection length within the subject through which X-ray travels (see, for example, JP-A-2005-095397).

The X-ray attenuation correction device 75 uses the boundary information obtained by the boundary information extracting device 74 to apply the correction for the amount of X-ray attenuation at the boundary position where the X-ray absorption rate is changing to the amount of scattered X-ray calculated by the scattered X-ray correction device 76. The X-ray attenuation correction device 75 has a gain function G (i, j) to be multiplied by the amount of scattered X-ray to correct for the amount of scattered X-ray. Now the gain function G (i, j) may be as follows, where f designates to a multidimensional function, $$G(i,j)=1+f[|D(i,j)|]$$

Then the amount of scattered X-ray S (i, j) for each channel number is multiplied by the gain function G (i, j), to yield the amount of scattered X-ray including the correction of X-ray attenuation at the boundary position. The gain function adjusts the magnitude of change and the amount of correction accordingly. The multidimensional function may be defined so as for the amount of correction to be experimentally optimum.

The X-ray attenuation correction device 75 then subtracts from the projection information the amount of scattered X-ray thus corrected to correct for the scattered X-ray. More Specifically, when the projection value after correction is CP (i, j), then $$CP(i,j)=P(i,j)-S(i,j)*G(i,j).$$

The corrected projection information CP (i, j) will be output to the image reconstruction device 72 for the image reconstruction.

Figure 4A:
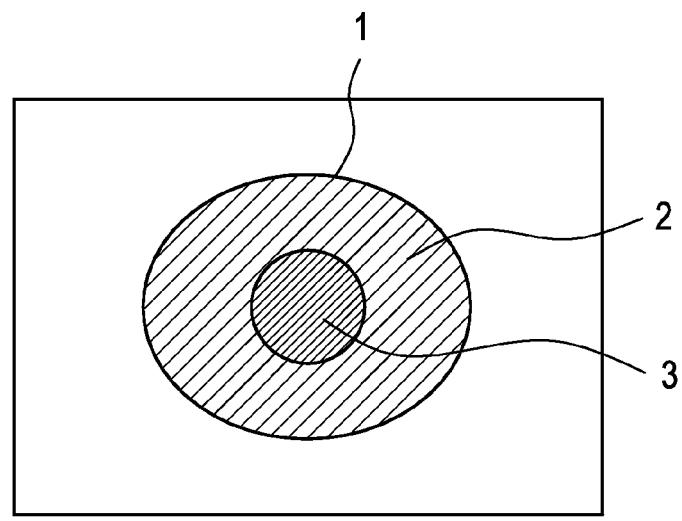
FIGS. 4a, 4b, and 4c are schematic diagrams illustrating the tomographic image, the projection information, and the boundary information of the subject 1.
Figure 4B:
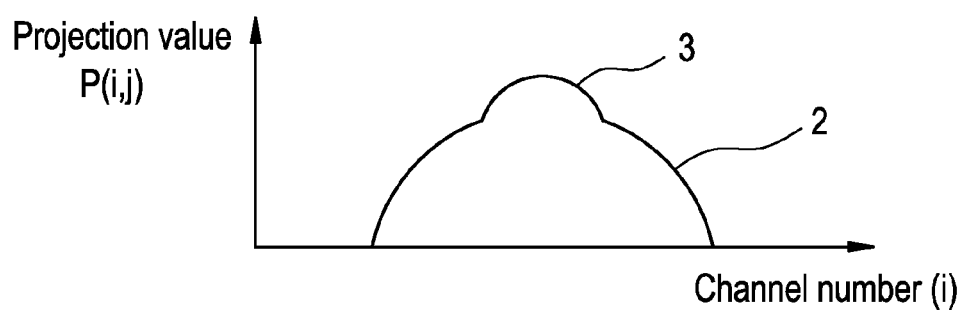
Figure 4C:
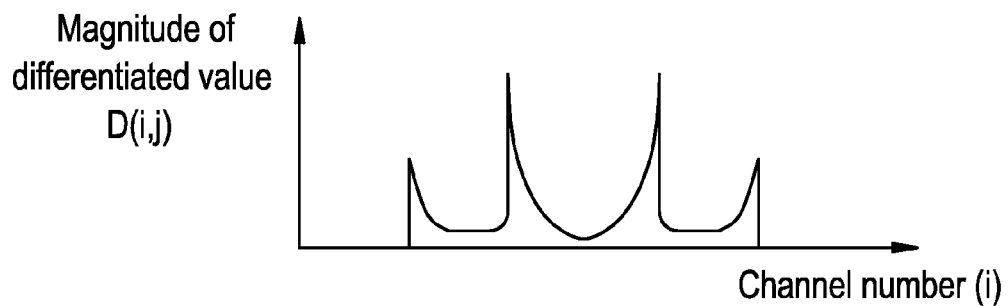

More specific operation of the X-ray attenuation correction by the data processing device 60 will be described in greater details with reference to FIG. 3. Now referring to FIG. 3, there is shown a flow chart indicating the operation of X-ray attenuation correction. First the operator places the subject 1 in the bore 29 to obtain the projection information of the subject 1 (step S301). FIG. 4 (A) shows schematically the cross-section of the subject 1 to be imaged. In the example shown in FIG. 4 (A), the subject 1 has a part of low X-ray absorption rate 2 in the elliptic shape and a part of high X-ray absorption rate 3 in the form of sphere residing in the vicinity of center of the elliptic part. FIG. 4 (B) indicates the projection information when the cross-section of the subject 1 shown in FIG. 4 (A) is projected in the vertical direction in the plane. The projection information has a projection image of the part of low X-ray absorption rate 2 in the shape of hemisphere in the channel direction, and in the vicinity of the center of the hemisphere the projection image of small hemispheric part including the part of high X-ray absorption rate 3. The projection information as described above may be obtained for each of view number (j) in correspondence with the rotational angle of the revolver unit 34 for 360 degrees surrounding the subject 1.

Thereafter, the boundary information extracting device 74 differentiate the projection information to extract the boundary position and the magnitude of change of the X-ray absorption rate, which are both boundary information (step S302). FIG. 4 (C) is an exemplary embodiment of differentiation of projection information shown in FIG. 4 (B) to determine the magnitude of the differentiated value. The value is large at the boundary position where the projection value of the projection information steeply changes.

Thereafter, the X-ray attenuation correction device 75 performs the correction for the amount of scattered X-ray S (i, j) calculated in the scattered X-ray correction device 76 for each view number and for each channel number (step S303). At this time the X-ray attenuation correction device 75 use the gain function to adjust the differentiated value, namely the magnitude of change of the X-ray absorption rate and the amount of correction to be multiplied by the amount of scattered X-ray.

Figure 5A:
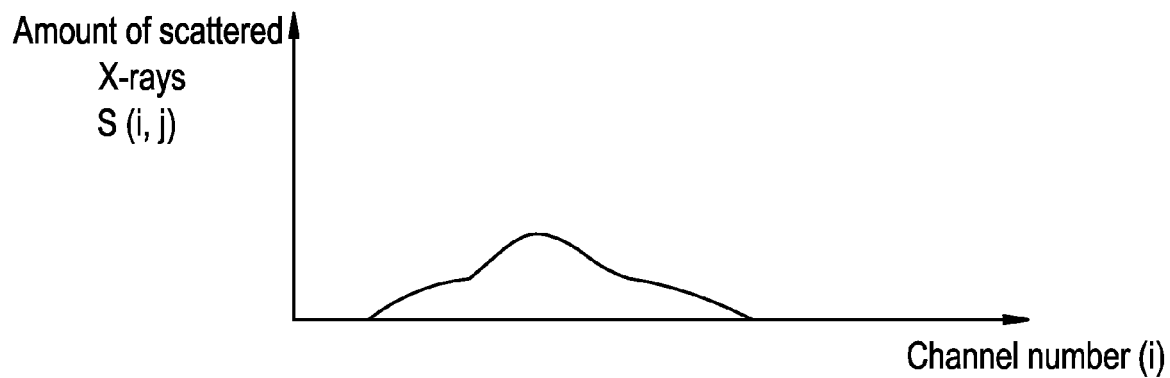
FIGS. 5a, 5b, and 5c are schematic diagrams illustrating the scattered X-ray information, the corrected scattered X-ray information, and the corrected projection value of the subject 1.
Figure 5B:
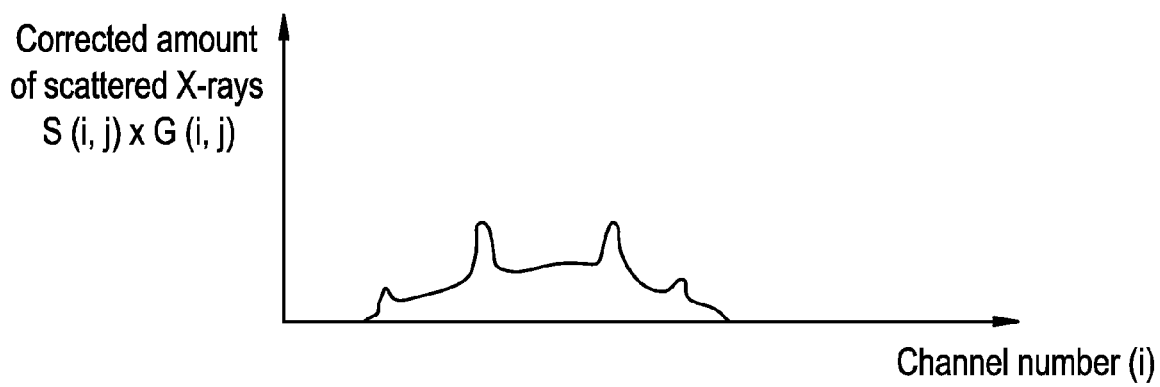
Figure 5C:
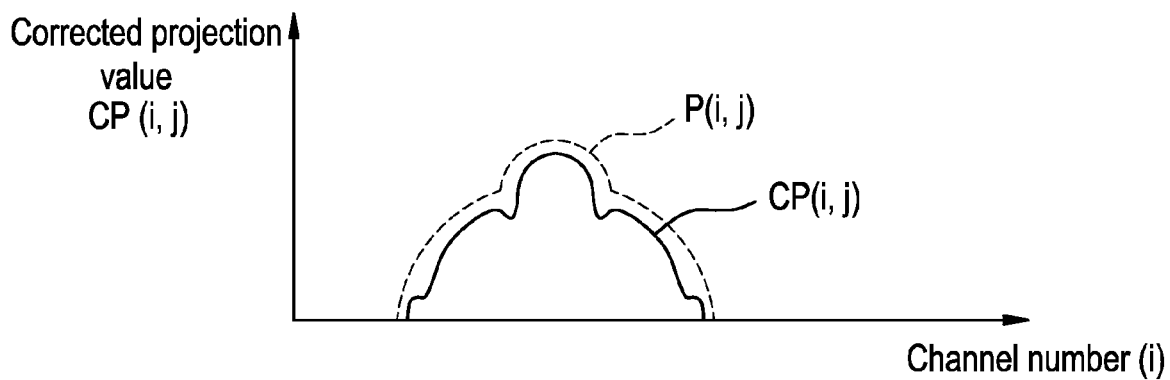

FIG. 5 (A) shows the amount of scattered X-ray S (i, j) calculated in the scattered X-ray correction device 76 and in the direction of projection of view number j similar to FIG. 4 (B), when the subject 1 has a cross-section as shown in FIG. 4 (A). The amount of scattered X-ray becomes a larger value at the position around the center where a part of high X-ray absorption rate 3 resides and the projection length is longer, and becomes a gradually smaller value at the periphery where the projection length is shorter. FIG. 5 (B) shows an example in which the magnitude of differentiated value |D (i, j)| at the position of channel direction as shown in FIG. 4 (C), namely the magnitude of change of the X-ray absorption rate is used to correct for the amount of scattered X-ray S (i, j). As there is some attenuation of X-ray at the boundary position of steeply changing projection value, the amount of scattered X-ray is considered to be sufficiently high.

Thereafter, the X-ray attenuation correction device 75 uses the amount of default pattern having been corrected for to perform a dispersion correction for the projection information (step S304). In the dispersion correction, the amount of scattered X-ray is subtracted from the projection value of projection information P (i, j). FIG. 5 (C) is an example of dispersion correction for the projection information of FIG. 4 (B) using the corrected amount of scattered X-ray S (i, j)×G (i, j) as shown in FIG. 5 (B). The solid line shown in FIG. 5 (C) indicates the projection information CP (i, j) which is corrected for the dispersion. The dotted line shown in FIG. 5 (C) indicates the projection information P (i, j) identical to that shown in FIG. 4 (B), for the purpose of comparison.

Thereafter, the image reconstruction device 72 uses the corrected projection information to perform image reconstruction (step S305), thus reconstructed tomographic image information will be displayed on the display device 68 (step S306).

As have been described above, in the first preferred embodiment of the present invention, the boundary information D (i, j) comprised of the boundary position of changing X-ray absorption rate and the magnitude of the change is extracted from the projection information P (i, j) of the subject 1, then the boundary information is used to multiply the amount G (i, j) corresponding to the magnitude of change at the boundary position by the amount of scattered X-ray S (i, j) to correct for the X-ray attenuation at the boundary position. The attenuation of X-ray at the boundary position is then corrected for along with the correction of scattered X-ray of projection information, to suppress the artifacts seen in a tomographic image.

Second Embodiment

In the first preferred embodiment described above, the projection information in the channel direction is differentiated to extract the boundary information of changing X-ray absorption rate. In the present preferred embodiment, an embodiment will be described in which the projection information in the direction corresponding to the row direction of the X-ray detector, which is the width of the direction perpendicular to the revolving direction of the X-ray detector (referred to as simply row direction herein below) is differentiated to extract the boundary information in the row direction. In this embodiment the boundary information extracting device 74 and the X-ray attenuation correction device 75 will be described in greater details and the description of other arrangements similar to the preceding preferred embodiment will be omitted.

In the present embodiment, the boundary information extracting device 74 has a differentiation device for differentiating the projection information in the row direction, and for determines the boundary position when the differentiated value exceeds a threshold. The magnitude of differentiated value Dk (i, k, j) may be given by $$|Dk(i,k,j)|=|[P(i,k+\Delta k,j)-P(i,k,j)]/\Delta k|$$

where P (i, k, j) is the projection value at the view number j and row number k, and given a threshold value th_k, the position of a row number $$|Dk(i,k,j)|>th\_k$$

will be determined as the boundary position.

The scattered X-ray correction device 76 calculates the amount of scattered X-ray S (i, k, j) for each view number, each channel number, and each row number, included in the projection information. The amount of default pattern S (i, k, j) may be calculated based on the scattered X-ray information obtained by using for example a phantom, in a manner similar to that in the preceding embodiment, to further improve the precision by taking into account the projection length and projection area within the subject of X-ray transmission.

The X-ray attenuation correction device 75 uses the boundary information obtained by the boundary information extracting device 74 to add further correction of the amount of X-ray attenuation at the boundary position of changing X-ray absorption rate for the amount of scattered X-ray calculated in the scattered X-ray correction device 76. The X-ray attenuation correction device 75 has a gain function G2 (i, k, j) to be multiplied by the amount of scattered X-ray to correct for the amount of scattered X-ray. Now the gain function is given as G2 (i, k, j), and f2 as a multidimensional function, $$G2(i,k,j)=1+f2[|Dk(i,k,j)|].$$

Then, the amount of scattered X-ray S (i, k, j) is multiplied by the gain function G2 (i, k, j), to obtain the amount of scattered X-ray including the correction for the X-ray attenuation at the boundary position. The gain function is for adjustment of the magnitude of change and the amount of corresponding correction. The multidimensional function may be determined experimentally so that the amount of correction becomes optimum.

In addition, the X-ray attenuation correction device 75 subtracts from the projection information the corrected amount of scattered X-ray to obtain the correction of scattered X-ray. In other words the projection value after correction is given as CP (i, k, j), $$CP(i,k,j)=P(i,k,j)-S(i,k,j)*G2(i,k,j).$$

The projection information CP (i, k, j) after correction will be output to the image reconstruction device 72 to perform the image reconstruction.

As can be seen from the foregoing, in the second preferred embodiment, the boundary information D (i, k, j) comprised of the boundary position of changing X-ray absorption rate and the magnitude of change from the projection information P (i, k, j) of the subject 1, then the boundary information is used to multiply the amount of scattered X-ray S (i, k, j) by the amount G2 (i, k, j) corresponding to the magnitude of change at the boundary position to correct for the X-ray attenuation at the boundary position. The X-ray attenuation at the boundary position of the projection information in the row direction can be corrected for together with the scattered X-ray correction of the projection information, allowing suppressing the artifacts seen in the tomographic image.

Third Embodiment

In the first preferred embodiment described above, the projection information in the channel direction is differentiated, and in the second preferred embodiment described above, the present invention in the row direction is differentiated, in order to extract the boundary information of changing X-ray absorption rate. In the present embodiment, an example will be described in which the projection information in both the channel direction and the row direction will be differentiated to extract the boundary information where the X-ray absorption rate is changing. In the preferred embodiment the boundary information extracting device 74 and the X-ray attenuation correction device 75 will be described in greater details, and other arrangement similar to those in the first embodiment will not be described.

In the present embodiment, the boundary information extracting device 74 has a differentiation device for differentiating the projection information in the channel direction and in the row direction, and for determining the boundary position when the differentiated value exceeds a threshold. Given the projection value at the position of view number j and row number k as P (i, k, j), the magnitude of differentiated value Di (i, k, j) in the channel direction and differentiated value Dk (i, k, j) in the row direction can be given by $$|Di(i,k,j)|=|[P(i+\Delta i,k,j)-P(i,k,j)]/\Delta i|,$$

$$|Dk(i,k,j)|=|[P(i,k+\Delta k,j)-P(i,k,j)]/\Delta k|.$$

The boundary position may be given from the position at row number $$|Di(i,k,j)|>th\_i$$

$$|Dk(i,k,j)|>th\_k,$$

where th_i is the threshold in the channel direction, th_k is the threshold in the row direction.

The scattered X-ray correction device 76 calculates the amount of scattered X-ray S (i, k, j) for each view number, each channel number, and each row number, included in the projection information. The amount of scattered X-ray S (i, k, j) is calculated based on the scattered X-ray information obtained by using for example a phantom in a manner similar to the first preferred embodiment, to further improve the precision by taking into account the projection length and projection area within the subject of X-ray transmission.

The X-ray attenuation correction device 75 uses the boundary information obtained by the boundary information extracting device 74 to apply correction for the amount of X-ray attenuation at the boundary position of changing the X-ray absorption rate to the amount of scattered X-ray calculated by the scattered X-ray correction device 76. Then the X-ray attenuation correction device 75 has a gain function G3 (i, k, j) to be multiplied by the amount of scattered X-ray for correcting for the amount of scattered X-ray. The gain function G3 (i, k, j), may be given by $$G3(i,k,j)=1+f3\,[|Di(i,k,j)|,\,|Dk(i,k,j)|],$$

where f3 is the multidimensional function. Then, the gain function G3 (i, k, j) is multiplied by the amount of scattered X-ray S(i, k, j) to determine the amount of scattered X-ray including the correction for the X-ray attenuation at the boundary position. The gain function adjusts the magnitude of change and the corresponding amount of correction. The multidimensional function may be defined experimentally so that the amount of correction becomes optimum.

In addition, the X-ray attenuation correction device 75 subtracts the corrected amount of scattered X-ray from the projection information to correct for the scattered X-ray. More specifically, given the projected value after correction CP (i, k, j), then $$CP(i,k,j)=P(i,k,j)-S(i,k,j)*G3(i,k,j).$$

then the corrected projection information CP (i, k, j) will be output to the image reconstruction device 72 for the image reconstruction.

As can be appreciated from the foregoing description, the third preferred embodiment extracts from the projection information P (i, k, j) of the subject 1 the boundary information D (i, k, j) comprised of the boundary position where the X-ray absorption rate is changing and the magnitude of change, then uses the boundary information to multiply amount of scattered X-ray S (i, k, j) by the amount G2 (i, k, j) corresponding to the magnitude of change at the boundary position, to correct for the X-ray attenuation at the boundary position. The X-ray attenuation at the boundary position of the projection information in the channel direction and in the row direction is corrected for along with the correction of scattered X-ray of the projection information, allowing thus suppressing the artifacts seen on the tomographic image.

Fourth Embodiment

In the first to third embodiments described above the projection information P (i, j) is differentiated to extract the boundary information D (i, j) where the X-ray absorption rate is changing, however, the boundary information may also be extracted from the tomographic image information having image reconstructed, to correct for the X-ray attenuation at the boundary position. In the fourth preferred embodiment of the invention, therefore, the boundary information is extracted from the tomographic image information having image reconstructed to apply correction for the X-ray attenuation at the boundary position where the X-ray absorption rate is changing.

Figure 6:
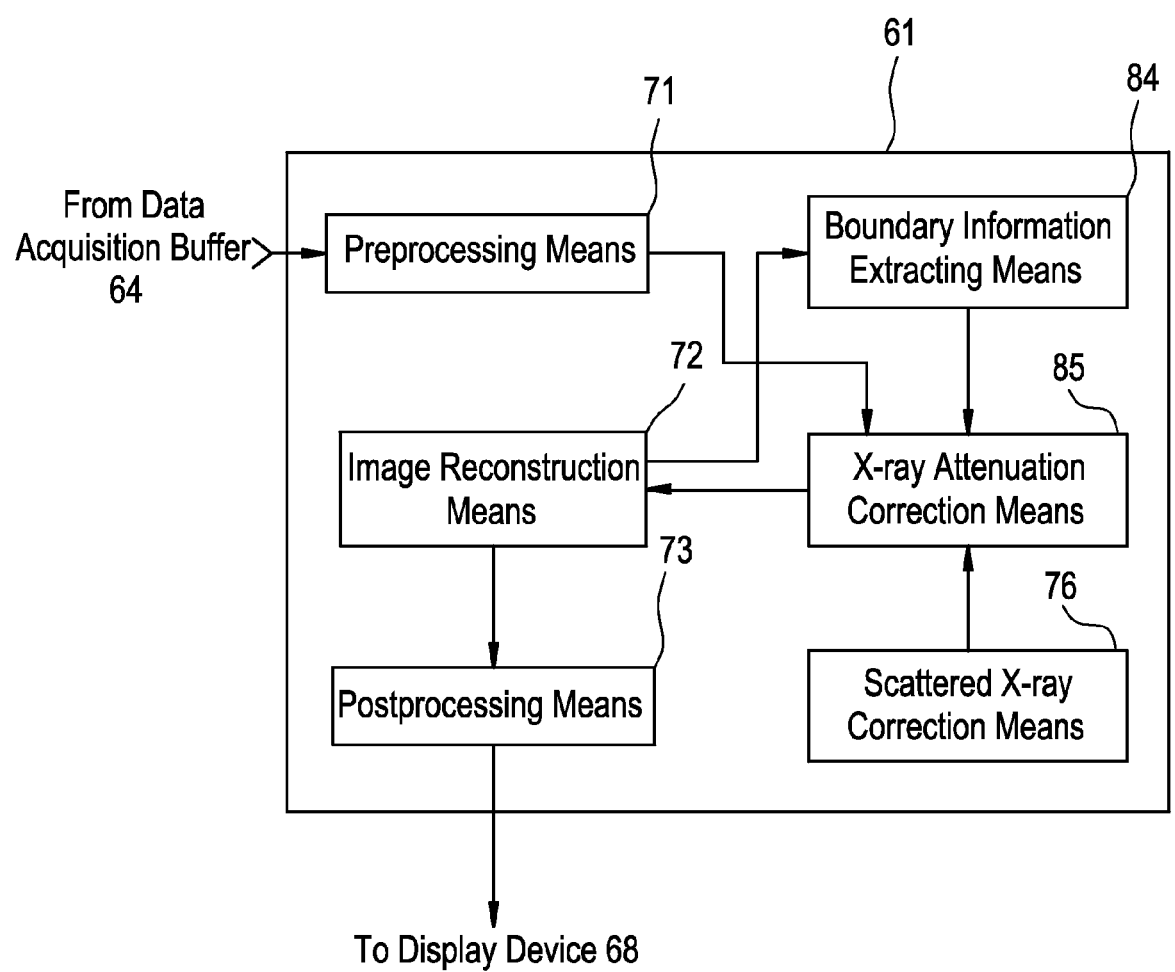
FIG. 6 is a functional schematic block diagram illustrating the functional arrangement of a data processing unit in accordance with fourth preferred embodiment of the present invention.

Now referring to FIG. 6 there is shown a schematic functional block diagram indicating the functional arrangement of a data processing unit 61 in accordance with the fourth preferred embodiment of the present invention. The data processing unit 61 corresponds to the data processing device 60 shown in the overview of FIG. 1, and the arrangement of other units are identical to that shown in FIG. 1, the detailed description thereof will be omitted.

The data processing unit 61 includes a preprocessing device 71, an image reconstruction device 72, a postprocessing device 73, a boundary information extracting device 84, an X-ray attenuation correction device 85, and a scattered X-ray correction device 76. The preprocessing device 71, the image reconstruction device 72, the postprocessing device 73, and the scattered X-ray correction device 76 are functionally identical to those shown in FIG. 2. Although in the first preferred embodiment, the preprocessing device 71 outputs the preprocessed projection information only to the boundary information extracting device 74, it outputs to the image reconstruction device 72 and to the X-ray attenuation correction device 85 in the fourth preferred embodiment. Then the image reconstruction device 72 uses the projection information supplied from the preprocessing device 71 to perform the image reconstruction to generate tomographic image information.

The boundary information extracting device 84 uses tomographic image information IMG (x, y) obtained from the image reconstruction device 72 (here x and y indicates the positional coordinates in horizontal and vertical direction of the image, respectively) to determine the boundary information comprised of the boundary position information of the boundary position where the X-ray absorption rate is discontinuously changing, and the magnitude information indicative of the magnitude of the change of the X-ray absorption rate at that boundary position. The boundary information extracting device 84 has a differentiating device for differentiating the tomographic image included in the tomographic image information, an absolute value device for generating a boundary image by determining the absolute value of the differentiated image, and a re-projection device for using the boundary image to determine a plurality of projected images from positions corresponding to every view angles.

To generate a boundary image BIMG (x, y) from the tomographic image IMG (x, y), following equation (1) will be used:

[Equation 1]

$$BIMG(x, y) = \left| \frac{IMG(x, y) * \mathrm{HF}(x, y)}{IMG(x, y) + 1000} \right| \quad (1)$$

In the above equation "*" is the convolution calculation, HF (x, y) is a filter function of the type high-pass. The numerator of the above equation constitutes the differentiating device described above, and the denominator of the above equation constitutes the normalization factor so as not to rely on the CT value.

Then the boundary information extracting device 84 determines the projection image BD (i, j) of the boundary image BIMG (x, y) for each view number and for each channel number. Then, when the projection image BD (i, j) has a projection value that is not zero, the boundary information extracting device 84 will determine the position in the channel direction with the projection value as the boundary position, and the magnitude of the projection value as the magnitude of change of the X-ray absorption rate.

The X-ray attenuation correction device 85 uses the boundary information obtained by the boundary information extracting device 84 to apply correction for the amount of X-ray attenuation at the boundary position where the X-ray absorption rate is changing to the amount of scattered X-ray calculated by the scattered X-ray correction device 76. The X-ray attenuation correction device 85 has a gain function to be multiplied by the amount of scattered X-ray, similar to the X-ray attenuation correction device 75, for correcting for the amount of scattered X-ray. The gain function may be expressed as $$G(i,j)=1+f[|BD(i,j)|]$$

where f is a multidimensional function. Now defining the amount of scattered X-ray as S (i, j), the amount of scattered X-ray corrected is, by definition, S (i,j)×G(i,j).

The X-ray attenuation correction device 85 subtracts the amount of scattered X-ray CP (i, j) thus corrected from the projection information P (i, j) from the preprocessing device 71 to correct for the scattered X-ray.

$$CP(i,j)=P(i,j)-S(i,j)\times G(i,j)$$

Figure 7:
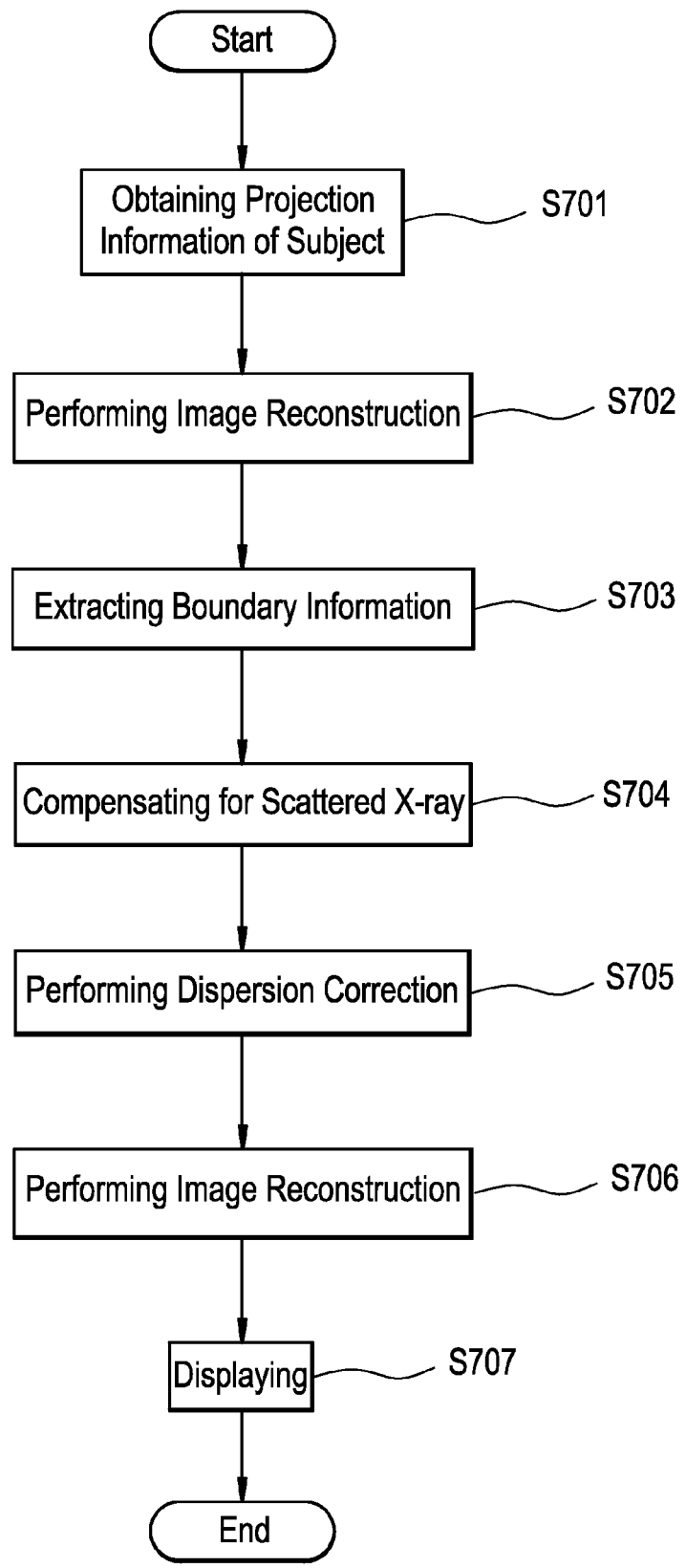
FIG. 7 is a flow chart illustrating the operation of X-ray attenuation correction in accordance with fourth preferred embodiment of the present invention.
Figure 8A:
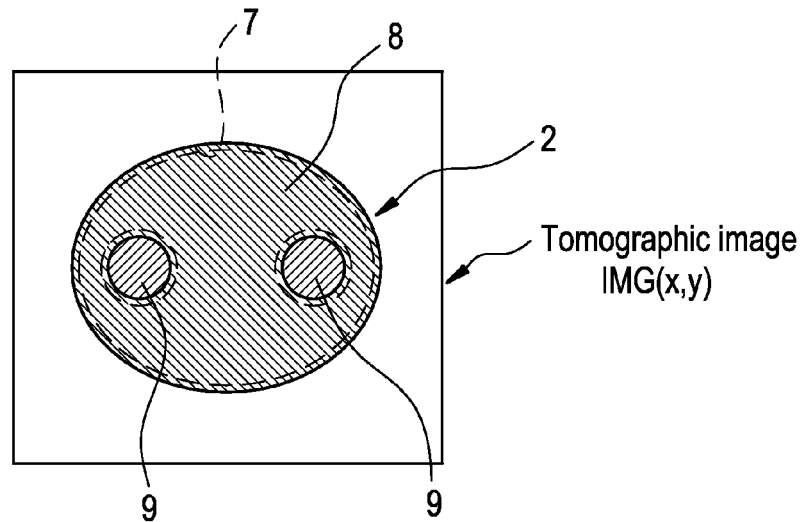
FIGS. 8a, 8b, and 8c are schematic diagrams illustrating the tomographic image, the boundary image, and the boundary projection value of the subject 2.
Figure 8B:
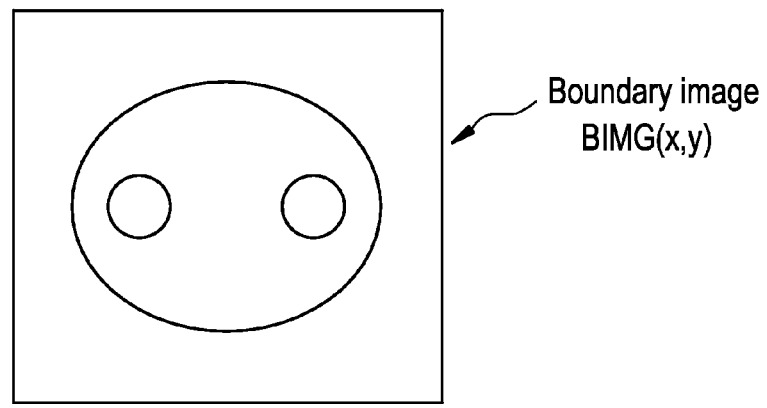
Figure 8C:
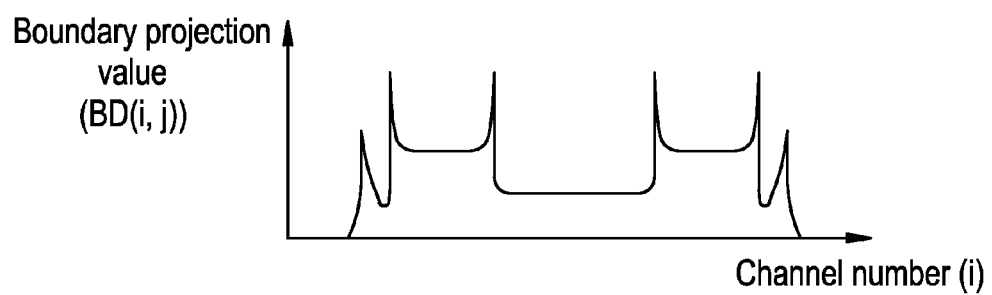

Next, more specific operation of the X-ray attenuation correction by the data processing unit 61 will be described in greater details with reference to FIG. 7. Now referring to FIG. 7, there is shown a flow chart indicative of the operation of the correction for attenuation of X-ray. At first the operator places a subject 2 within the bore 29 to obtain the projection information of the subject 2 (step S701). The projection information is transmitted to the data processing unit 61, then preprocessed in the preprocessing device 71, then output to the image reconstruction device 72. Then the image reconstruction device 72 will perform the image reconstruction of the projection information P (i, j) (step S702), to obtain the tomographic image information IMG (x, y). FIG. 8 (A) shows an example of tomographic image from the subject 2. The tomographic image shown incorporates a part of low X-ray absorption 8, which is the majority of the subject 2, and two circular parts of high X-ray absorption 9 within the low X-ray absorption part 8. The part shown by dotted line in the tomographic image indicates schematically an artifact 7 generated by the X-ray attenuation at the boundary position where the X-ray absorption rate is changing.

Now returning to FIG. 7, the data processing unit 61 extracts the boundary information using the boundary information extracting device 84 (step S703). In the extraction of boundary information, an operation using the equation (1) is performed on the tomographic image IMG (x, y), to determine the boundary image BIMG (x, y). FIG. 8 (B) shows a boundary image determined from the tomographic image shown in FIG. 8 (A). In the figure the boundary area between the low X-ray absorption part 8 and the high X-ray absorption part 9 of the subject 2 is extracted. Then the boundary information extracting device 84 calculates boundary projection value BD (i, j), which is the boundary information for each view number and for each channel number, from the boundary image BIMG (x, y). FIG. 8 (C) shows an example of boundary projection value, which is projected in the vertical direction within the plane of boundary image shown in FIG. 8 (B). In FIG. 8 (C) the boundary projection value is larger at the periphery of the low X-ray absorption part 8 and at the periphery of the high X-ray absorption part 9, and the boundary projection value including the high X-ray absorption part 9 indicates a larger value than the boundary projection value comprised of the low X-ray absorption part 8.

Now returning to FIG. 7, the data processing unit 61 uses the X-ray attenuation correction device 85 to correct for the amount of scattered X-ray (step S704). In this correction, a gain function G (i, j) is determined using the boundary projection value BD (i, j), then the gain function G (i, j) is multiplied by the amount of scattered X-ray S (i, j).

Figure 9A:
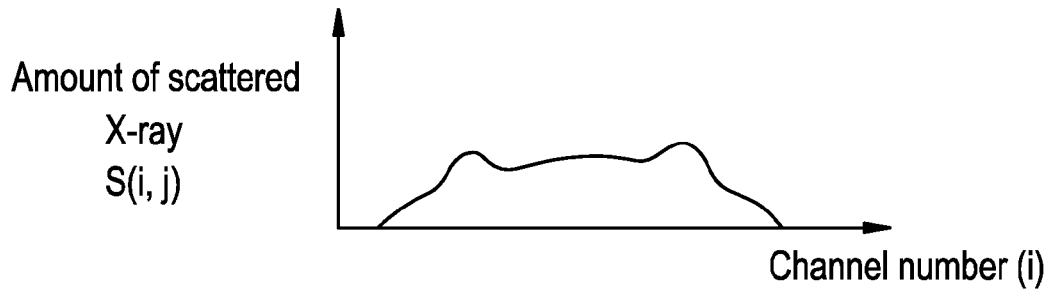
FIGS. 9a, 9b, and 9c are schematic diagrams illustrating scattered X-ray information, the corrected scattered X-ray information, and the corrected projection value of the subject 2.
Figure 9B:
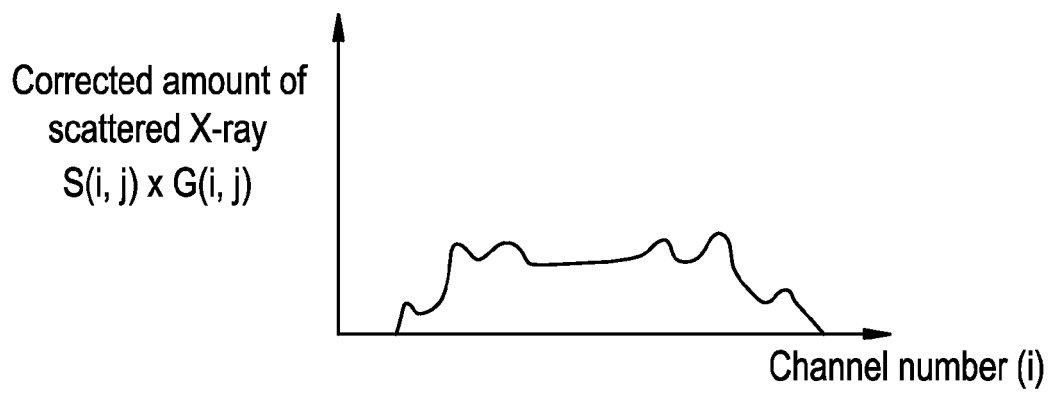
Figure 9C:
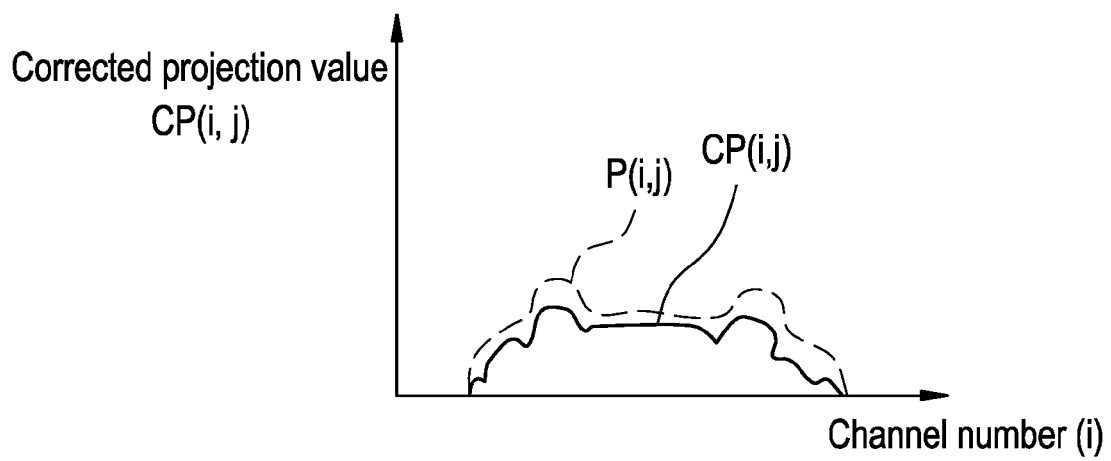

FIG. 9 (A) shows the amount of scattered X-ray S (i, j) in the vertical direction of the subject 2, determined by the scattered X-ray correction device 76. FIG. 9 (B) shows the corrected amount of scattered X-ray by multiplying the amount of scattered X-ray S (i, j) by the gain function G (i, j) of the boundary projection value BD (i, j).

Now returning to FIG. 7, the data processing unit 61 uses the X-ray attenuation correction device 85 to perform dispersion correction (step S705). In the dispersion correction, the X-ray attenuation correction device 85 subtracts the corrected amount of scattered X-ray S (i, j)×G (i, j) from the projection information P (i, j) of the subject 2 obtained from the preprocessing device 71. FIG. 9 (C) shows the projection information P (i, j) of the subject 2 by the dotted line in the figure, and the projection information CP (i, j) of the subject 2 with dispersion correction by the solid line in the figure.

Now returning to FIG. 7, the data processing unit 61 uses the image reconstruction device 72 to perform the image reconstruction from the projection information CP (i, j) with dispersion correction operated (step S706), then displays thus reconstructed image on the display device 68 (step S707). In the reconstructed image the artifact 7 as shown in the tomographic image of FIG. 8 (A) is to be alleviated.

As can be appreciated from the foregoing description, in the present second embodiment, the boundary image BIMG (x, y) comprised of only boundary position where the X-ray absorption rate is changing is extracted from the tomographic image IMG (x, y) of the subject 2, then the boundary projection value BD (i, j) of the boundary image is calculated for each view number and for each channel number, then the boundary projection value is used to correct for the amount of scattered X-ray S (i, j), then the amount of scattered X-ray is used to perform the dispersion correction of the projection information P (i, j) of the subject 2. The attenuation of X-ray at the boundary position where the X-ray absorption rate is changing is corrected for along with the dispersion correction of the projection information, allowing alleviating the artifact 7 developed in the tomographic image.

Fifth Embodiment

In the fourth preferred embodiment described above, the boundary image BIMG (x, y) is extracted from the tomographic image, then the boundary projection value BD (i, j) of the boundary image is used to correct for the projection information of the subject 2. The scattered X-ray and artifacts may alternatively alleviated by image reconstruction of the amount of scattered X-ray corrected based on the boundary projection value to generate scattered X-ray image, and then by subtracting the scattered X-ray image from the tomographic image. In the fifth preferred embodiment of the present invention, scattered X-ray image corrected for by the boundary projection value is used to correct for the X-ray attenuation at the boundary position where the X-ray absorption rate of the tomographic image is changing.

Figure 10:
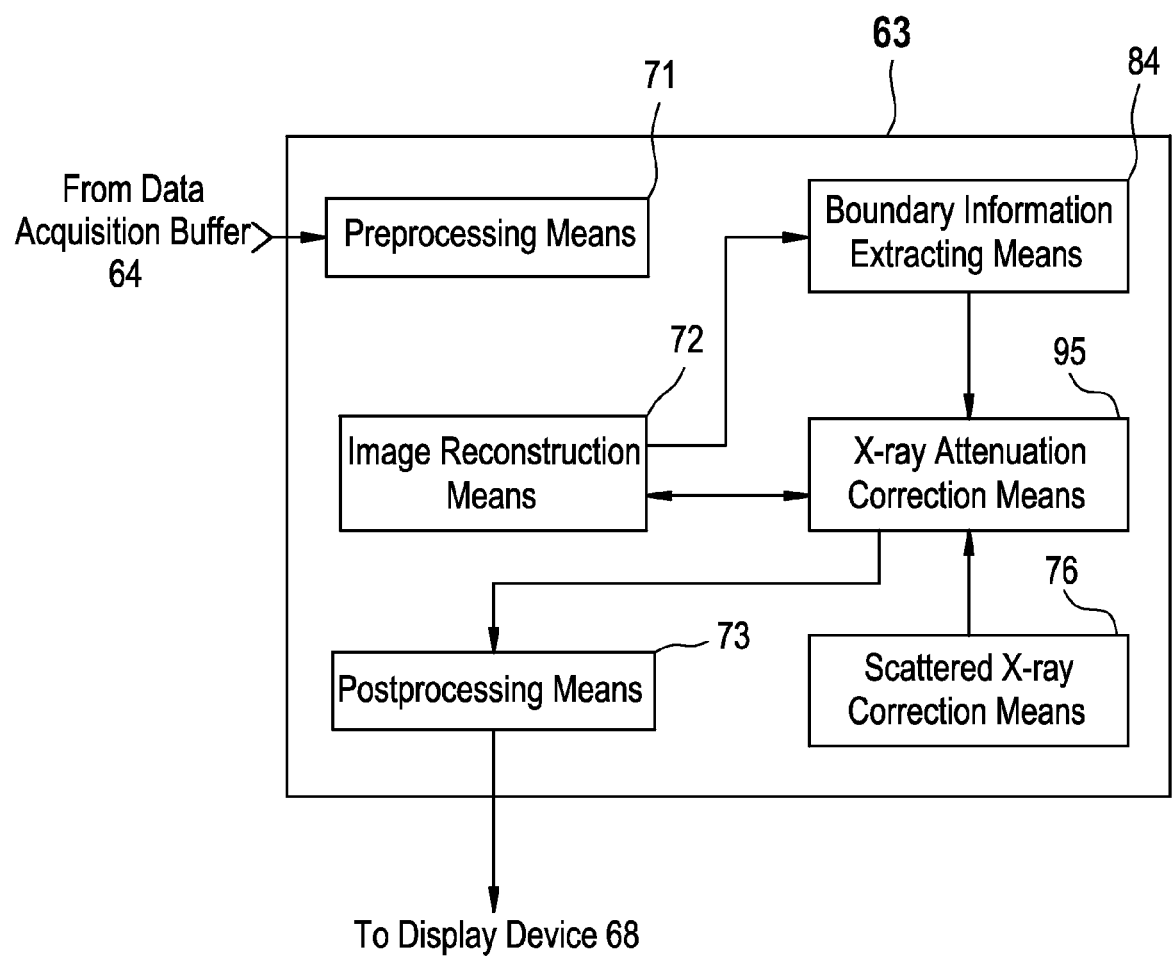
FIG. 10 is a functional schematic block diagram illustrating the functional arrangement of a data processing unit in accordance with fifth preferred embodiment of the present invention.

Now referring to FIG. 10, there is a functional schematic block diagram illustrating a functional arrangement of a data processing unit 63 in accordance with the fifth preferred embodiment of the present invention. The data processing unit 63 corresponds to the data processing device 60 shown in the overview of FIG. 1, and other arrangements are identical to those shown in FIG. 1, detailed description thereof will be omitted.

The data processing unit 63 includes a preprocessing device 71, an image reconstruction device 72, a postprocessing device 73, a boundary information extracting device 84, an X-ray attenuation correction device 95, and a scattered X-ray correction device 76. The preprocessing device 71, the image reconstruction device 72, the postprocessing device 73, the boundary information extracting device 84, and the scattered X-ray correction device 76 are functionally identical to those of the fourth preferred embodiment as shown in FIG. 6, thus detailed description thereof will be omitted. However, in the fifth preferred embodiment of the present invention, the preprocessing device 71 will not output the preprocessed projection information to the X-ray attenuation correction device 95, the X-ray attenuation correction device 95 uses only the tomographic image and scattered X-ray image having image reconstruction performed, to correct for the X-ray attenuation at the boundary position. The image reconstruction device 72 will not output a reconstructed image directly to the 078, rather it will output thereto through the X-ray attenuation correction device 95.

Figure 11A:
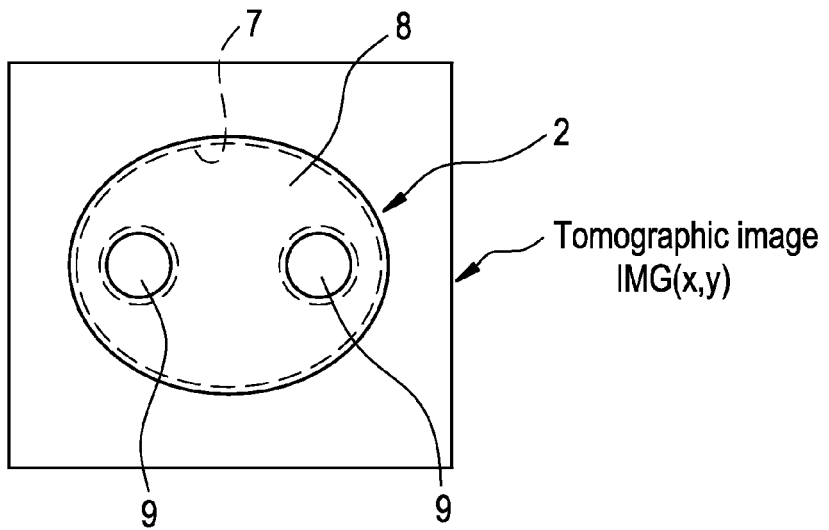
FIGS. 11a, 11b, and 11c are schematic diagrams illustrating the tomographic image, the scattered X-ray image, and the subtracted image of the subject 2.
Figure 11B:
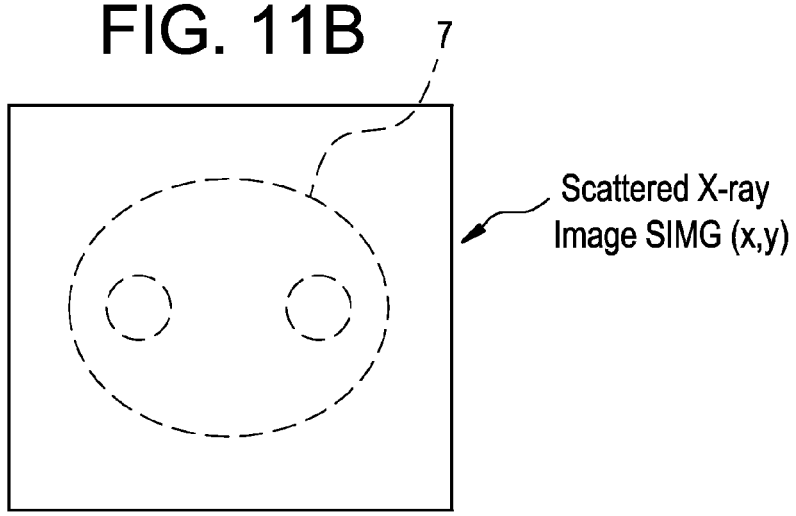
Figure 11C:
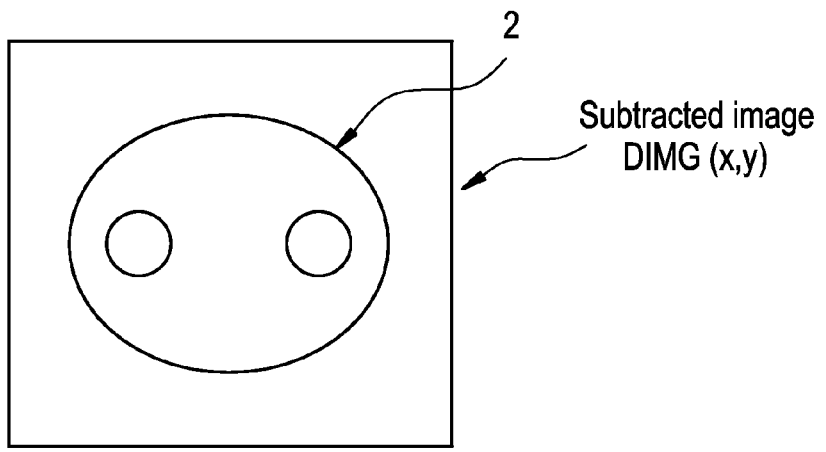

Now referring to FIG. 11 (A), there is shown an example of tomographic image IMG (x, y) to be image reconstructed from the projection information of the subject 2. The subject 2 has a low X-ray absorption part 8 and two circular high X-ray absorption parts 9 therewithin. On the periphery of the low X-ray absorption part 8 and the high X-ray absorption part 9 some artifacts 7 are shown by dotted line.

The X-ray attenuation correction device 95, in a manner similar to the X-ray attenuation correction device 85, uses the boundary projection value BD (i, j) obtained from the boundary image BIMG (x, y) from the boundary information extracting device 84 to correct for the amount of scattered X-ray S (i, j) being calculated by the scattered X-ray correction device 76. To generate a boundary image BIMG (x, y) from the tomographic image IMG (x, y), the following equation (2) is used:

[Equation 2]

$$BIMG(x,y) = |IMG(x,y) * HF(x,y)| \qquad (2)$$

In the equation "*" is the convolution computation, and HF (x, y) is a filter function of the type high-pass. The boundary projection value BD (i, j) is converted by using a gain function G (i, j) as similar to the X-ray attenuation correction device 85.

Thereafter, the X-ray attenuation correction device 95 outputs to the image reconstruction device 72 the corrected amount of scattered X-ray S (i, j)×G (i, j). The image reconstruction device 72 then performs image reconstruction of the corrected amount of scattered X-ray to generate a scattered X-ray image SIMG (x, y). FIG. 11 (B) shows a schematic diagram of the scattered X-ray image having image reconstruction performed thereon. This image is a visualization of artifact 7 part shown in FIG. 11 (A).

Thereafter, the X-ray attenuation correction device 95 inputs the scattered X-ray image SIMG (x, y) from the image reconstruction device 72, performs a subtraction with the tomographic image IMG (x, y) to generate a subtraction image DIMG (x, y). More specifically, it calculates $$DIMG(x,y) = IMG(x,y) - SIMG(x,y)$$

FIG. 11 (C) shows a subtracted subtraction image. The subtraction image is an image made with the artifact 7 part being eliminated from the tomographic image.

Thereafter, the X-ray attenuation correction device 95 outputs the subtraction image to the postprocessing device 73, and the postprocessing device 73 outputs this subtraction image to the display device 68 after the postprocessing.

As can be appreciated from the foregoing description, in the fifth preferred embodiment of the present invention, the boundary projection value BP (i, j) for each view number and each channel number is calculated from the boundary image BIMG (x, y) comprised of only the boundary of the tomographic image IMG (x, y) of the subject 2, then the boundary projection value is used to correct for the amount of scattered X-ray S (i, j), then by the image reconstruction of the amount of scattered X-ray a scattered X-ray image SIMG (x, y) is generated, thereafter the tomographic image is subtracted with it. The attenuation of X-ray at the boundary position where the X-ray absorption rate is changing may be corrected for along with the subtraction of scattered X-ray image, allowing alleviating the artifact 7 developed in the tomographic image.

The invention claimed is:

1. An X-ray attenuation correction method comprising steps of:
    extracting boundary information including boundary positional information of a boundary position where X-ray absorption rate is changing and magnitude information indicative of magnitude of said change, by using X-ray projection information of a subject or tomographic image information being generated by image reconstruction of said projection information; and
    correcting X-ray attenuation of said boundary position included in said projection information or said tomographic image information by using said boundary information.

2. An X-ray attenuation correction method according to claim 1, wherein
    said step of extracting boundary information includes steps of:
    differentiating projection value of said projection information in the direction corresponding to the channel direction and/or row direction of an X-ray detector which obtains said projection information;
    extracting a position where the magnitude of said differentiated value exceeds a threshold as said boundary position information; and
    extracting the magnitude of said differentiated value as said magnitude information.

3. An X-ray attenuation correction method according to claim 1, wherein
    said step of extracting boundary information includes steps of:
    differentiating the tomographic image of said tomographic image information;
    performing absolute value operation of said differentiated image to generate a boundary image; and
    extracting said boundary information using said boundary image.

4. An X-ray attenuation correction method according to claim 3, wherein
    said step of extracting boundary information includes the steps of:
    calculating boundary projection information using said boundary image;
    extracting as boundary position information a position where the boundary projection value of said boundary projection information is not zero; and
    extracting said boundary projection value as said magnitude information.

5. An X-ray attenuation correction method according to claim 1, wherein
    said step of correcting X-ray attenuation includes a step of correcting by using a gain function having a multidimensional function of said projection information.

6. An X-ray attenuation correction method according to claim 5, wherein
    said step of correcting X-ray attenuation includes steps of multiplying the amount of scattered X-ray at said boundary position in said projection information by the function value of said gain function, then subtracting said multiplied amount of scattered X-ray from said projection information.

7. An X-ray attenuation correction method according to claim 5, wherein
    said step of correcting X-ray attenuation includes steps of multiplying the amount of scattered X-ray at said boundary position in said tomographic image information by the function value of said gain function, performing image reconstruction of said multiplied amount of scattered X-ray, and then subtracting the amount from said tomographic image information.

8. An image generating apparatus for generating a tomographic image for an X-ray CT apparatus, comprising:
    a device for extracting boundary information including boundary position information of the boundary position where X-ray absorption rate is changing and magnitude information indicative of magnitude of said change, by using X-ray projection information of a subject or tomographic image information generated by performing image reconstruction of said projection information; and a device for correcting X-ray attenuation of said boundary position included in said projection information or said tomographic image information by using said boundary information.

9. An image generating apparatus according to claim 8, wherein said device for extracting boundary information includes a device for differentiating a projection value of said projection information in the direction corresponding to the channel direction and/or row direction of an X-ray detector which obtains said projection information, and a device for extracting a position where the magnitude of said differentiated value exceeds a threshold as said boundary position information.

10. An image generating apparatus according to claim 8, wherein said device for extracting boundary information includes a device for differentiating a tomographic image of said tomographic image information, a device for performing the absolute value operation on said differentiated image to generate a boundary image, and a device for extracting said boundary information by using said boundary image.

11. An image generating apparatus according to claim 10, wherein said device for extracting boundary information includes a device for calculating boundary projection information by using said boundary image, a device for extracting as boundary position information a position where boundary projection value of said boundary projection information is not zero, and a device for extracting said boundary projection value as said magnitude information.

12. An image generating apparatus according to claim 8, wherein said device for correcting X-ray attenuation includes a device for correcting by using a gain function having a multidimensional function of said magnitude information.

13. An image generating apparatus according to claim 12, wherein said device for correcting X-ray attenuation includes a device for correcting by multiplying the amount of scattered X-ray at said boundary position in said projection information by a function value of said gain function, and subtracting said multiplied amount of scattered X-ray from said projection information.

14. An image generating apparatus according to claim 12, wherein said device for correcting X-ray attenuation includes a device for correcting by multiplying the amount of scattered X-ray at said boundary position in said tomographic image information by a function value of said gain function, performing image reconstruction of said multiplied amount of scattered X-ray, and subtracting the amount from said tomographic image information.

15. An X-ray CT apparatus comprising:

an X-ray data acquisition device including an X-ray generator and an X-ray detector placed in opposition to said X-ray generator for acquiring X-ray projection data by relatively rotating said X-ray generator and said X-ray detector around a subject; and an image information generating device for generating image information of the subject using said X-ray projection data;

wherein said image information generating device includes:

a device for extracting boundary information including boundary position information of the boundary position where X-ray absorption rate is changing and magnitude information indicative of magnitude of said change, by using X-ray projection information of a subject or tomographic image information generated by performing image reconstruction of said projection information; and a device for correcting X-ray attenuation of said boundary position included in said projection information or said tomographic image information by using said boundary information.

16. An X-ray CT apparatus according to claim 15, wherein said device for extracting boundary information includes a device for differentiating a projection value of said projection information in the direction corresponding to the channel direction and/or row direction of an X-ray detector which obtains said projection information, and a device for extracting a position where the magnitude of said differentiated value exceeds a threshold as said boundary position information.

17. An X-ray CT apparatus according to claim 15, wherein said device for extracting boundary information includes a device for differentiating a tomographic image of said tomographic image information, a device for performing the absolute value operation on said differentiated image to generate a boundary image, and a device for extract said boundary information using said boundary image.

18. An X-ray CT apparatus according to claim 17, wherein said device for extracting boundary information includes a device for calculating boundary projection information by using said boundary image, a device for extracting as boundary position information a position where boundary projection value of said boundary projection information is not zero, and a device for extracting said boundary projection value as said magnitude information.

* * * * *